US012751365B2

(12) United States Patent
Pfléderer et al.

(10) Patent No.: US 12,751,365 B2
(45) Date of Patent: Oct. 6, 2026

(54) APPARATUS AND SYSTEM FOR ANALYZING AGRICULTURAL MATERIAL

(71) Applicant: Deere & Company, Moline, IL (US)

(72) Inventors: Wilson Pflederer, Davenport, IA (US); Douglas G. Temple, Fulton, IL (US); Candace M. Sunken, Dixon, IA (US); Nithin C. Choudary, Bettendorf, IA (US)

(73) Assignee: Deere & Company, Moline, IL (US)

( * ) Notice: Subject to any disclaimer, the term of this patent is extended or adjusted under 35 U.S.C. 154(b) by 524 days.

(21) Appl. No.: 18/312,905

(22) Filed: May 5, 2023

(65) Prior Publication Data

US 2024/0365706 A1 Nov. 7, 2024

(51) Int. Cl.

| | |
|---|---|
| ***A01D 41/127*** | (2006.01) |
| ***A01D 61/00*** | (2006.01) |
| ***G01N 21/85*** | (2006.01) |
| ***G01N 33/00*** | (2006.01) |

(52) U.S. Cl.
CPC ......... *A01D 41/1277* (2013.01); *A01D 61/00* (2013.01); *G01N 33/0098* (2013.01); *G01N 2021/8592* (2013.01)

(58) Field of Classification Search
CPC ............ A01D 41/1277; A01D 41/1272; A01D 61/00; A01D 43/085
See application file for complete search history.

(56) References Cited

U.S. PATENT DOCUMENTS 5,560,246 A * 10/1996 Bottinger ............. A01D 41/127 73/861.73
5,616,851 A 4/1997 Mcmahon et al.
6,119,531 A 9/2000 Wendte et al.
(Continued)

FOREIGN PATENT DOCUMENTS

CN 115372355 A 11/2022
EP 1518452 A1 3/2005
(Continued)

OTHER PUBLICATIONS

JP_H10282028_A_-_English_translation (Year: 1998).*
(Continued)

*Primary Examiner* — Christopher J Sebesta
*Assistant Examiner* — Julia C Tran
(74) *Attorney, Agent, or Firm* — Harness, Dickey & Pierce, P.L.C.

(57) ABSTRACT

An apparatus for analyzing agricultural material includes a housing defining an inlet adjacent a first end of the housing and configured to receive the agricultural material, a first chamber coupled to the inlet, a first outlet coupled to the first chamber, a second chamber coupled to the first chamber, a funnel portion between the first chamber and the second chamber, and a second outlet adjacent a second end of the housing and coupled to the second chamber. The second chamber includes a metering conveyor. The apparatus includes a first sensor coupled to a first side of the housing. The first sensor may include a camera. At least one second sensor may be coupled to a second side of the housing. The at least one second sensor includes one or more of a moisture sensor, a near-infrared (NIR) sensor, a temperature sensor, a capacitive sensor, and a proximity sensor.

19 Claims, 12 Drawing Sheets

(56) References Cited

U.S. PATENT DOCUMENTS

| | | | | |
|---|---|---|---|---|
| 6,155,103 | A * | 12/2000 | Diekhans | A01D 41/1277 73/863.52 |
| 6,285,198 | B1 * | 9/2001 | Nelson | A01D 41/1277 73/335.04 |
| 6,437,582 | B1 * | 8/2002 | Rode | A01D 41/1277 73/335.04 |
| 6,845,326 | B1 * | 1/2005 | Panigrahi | A01D 41/1277 356/73.1 |
| 11,224,158 | B2 * | 1/2022 | Hubalek | A01C 23/007 |
| 2002/0133309 | A1 * | 9/2002 | Hardt | A01D 41/1277 702/129 |
| 2003/0063276 | A1 * | 4/2003 | Sjodin | A01D 41/1277 356/326 |
| 2009/0258684 | A1 * | 10/2009 | Missotten | G01N 21/55 460/5 |
| 2009/0291723 | A1 | 11/2009 | Missotten | |
| 2015/0271988 | A1 | 10/2015 | Gray et al. | |
| 2017/0045444 | A1 * | 2/2017 | Haiges | G01N 21/359 |
| 2017/0049050 | A1 * | 2/2017 | Lenaerts | G01N 33/10 |
| 2017/0112056 | A1 | 4/2017 | Sierra et al. | |
| 2017/0112057 | A1 * | 4/2017 | Loukili | A01D 41/127 |
| 2018/0059034 | A1 | 3/2018 | Advani et al. | |
| 2020/0077583 | A1 | 3/2020 | Vandike et al. | |
| 2020/0084967 | A1 | 3/2020 | Corban et al. | |
| 2020/0333278 | A1 | 10/2020 | Locken et al. | |
| 2020/0394580 | A1 * | 12/2020 | Bull | G06Q 10/06 |
| 2021/0192715 | A1 * | 6/2021 | Leshem | B07C 5/3425 |
| 2022/0375115 | A1 * | 11/2022 | Missotten | G06T 7/0004 |
| 2022/0412936 | A1 | 12/2022 | Culpepper et al. | |
| 2023/0172105 | A1 * | 6/2023 | Brune | A01D 61/008 460/7 |

FOREIGN PATENT DOCUMENTS

| | | | |
|---|---|---|---|
| EP | 2168419 | A1 | 3/2010 |
| EP | 2927675 | A1 | 10/2015 |
| EP | 3038054 | A2 | 6/2016 |
| EP | 3133389 | A1 | 2/2017 |
| EP | 3158849 | A1 | 4/2017 |
| EP | 3159827 | A1 | 4/2017 |
| JP | H10282028 | A * | 10/1998 |
| WO | WO 2006010761 | A1 | 2/2006 |

OTHER PUBLICATIONS

U.S. Appl. No. 18/312,841, filed May 5, 2023.

Non-Final Office Action for U.S. Appl. No. 18/312,841, dated Sep. 26, 2025, 29 pages.

Notice of Allowance regarding U.S. Appl. No. 18/312,905 dated Mar. 31, 2026.

* cited by examiner

APPARATUS AND SYSTEM FOR ANALYZING AGRICULTURAL MATERIAL

FIELD

The present disclosure relates to an apparatus and system for analyzing agricultural material during a harvesting operation.

BACKGROUND

Some agricultural machines include a bypass coupled to a grain elevator for receiving at least a portion of agricultural material harvested by the agricultural machine.

SUMMARY

At least one example embodiment relates to an apparatus for analyzing agricultural material. The apparatus includes a housing defining an inlet adjacent a first end of the housing and configured to receive the agricultural material, a first chamber coupled to the inlet, a first outlet coupled to the first chamber, a second chamber coupled to the first chamber, a funnel portion between the first chamber and the second chamber, and a second outlet adjacent a second end of the housing and coupled to the second chamber. The second chamber includes a metering conveyor.

In at least one example embodiment, the apparatus includes a first sensor coupled to a first side of the housing.

In at least one example embodiment, the first sensor includes a camera.

In at least one example embodiment, at least one second sensor is coupled to a second side of the housing.

In at least one example embodiment, the at least one second sensor includes one or more of a moisture sensor, a near-infrared (NIR) sensor, a temperature sensor, a capacitive sensor, and a proximity sensor.

In at least one example embodiment, the apparatus includes a wall extending along at least a portion of the metering conveyor from a first side towards a second side of the housing. The funnel portion is defined by at least a portion of the wall.

In at least one example embodiment, the first chamber is upstream of the second chamber.

In at least one example embodiment, a width of the funnel portion tapers between the first chamber and the second chamber.

In at least one example embodiment, the housing is configured to separate the agricultural material into a first flow and a second flow. The first flow includes a first density and the second flow includes a second density. The first density is greater than the second density.

In at least one example embodiment, housing is configured to direct the first flow of the agricultural material along a first side of the housing; and In at least one example embodiment, housing is configured to direct the second flow of the agricultural material along a second first side of the housing opposite the first side.

In at least one example embodiment, the housing is configured to direct the agricultural material within the first chamber on a first side of the housing towards the second outlet at an increased rate compared to the agricultural material on a second side of the housing opposite the first side.

In at least one example embodiment, the first outlet is coupled to the second outlet.

In at least one example embodiment, the metering conveyor includes a metering wheel, an auger, or a roller.

At least one example embodiment relates to a system for analyzing agricultural material. The system includes an elevator and a first housing coupled to the elevator. The elevator includes a first side and a second side. The elevator extends from a first end to a second end. The first end of the elevator includes a receptacle formed between the first side and the second side. The receptacle is configured to receive the agricultural material. The first housing defines a first inlet configured to receive at least a portion of the agricultural material. The first housing includes a first chamber coupled to the first inlet, a first outlet coupled to the first chamber, a second chamber coupled to the first chamber, a first funnel portion between the first chamber and the second chamber, and a second outlet coupled to the second chamber. The second chamber includes a first metering conveyor, In at least one example embodiment, the elevator includes a plurality of paddles configured to deliver at least a portion of the agricultural material from the receptacle to the first inlet of the first housing via the first side of the elevator.

In at least one example embodiment, the system includes a first sensor coupled to a first side of the first housing.

In at least one example embodiment, the first sensor includes a camera.

In at least one example embodiment, the system includes at least one second sensor coupled to a second side of the first housing.

In at least one example embodiment, the at least one second sensor includes one or more of a moisture sensor, a near-infrared (NIR) sensor, a temperature sensor, a capacitive sensor, and a proximity sensor.

In at least one example embodiment, the first outlet and the second outlet are configured to direct at least a portion of the agricultural material to the receptacle of the elevator.

In at least one example embodiment, the first funnel portion is defined by at least a portion of a wall of the first housing extending along at least a portion of the first metering conveyor from a first side of the first housing towards a second side of the first housing opposite the first side.

In at least one example embodiment, the first housing is configured to separate the agricultural material into a first flow and a second flow. The first flow includes a first density and the second flow includes a second density. The first density is greater than the second density. The first housing is configured to direct the first flow of the agricultural material along a first side of the first housing. The first housing is configured to direct the second flow of the agricultural material along a second side of the first housing opposite the first side. The first housing is configured to direct the agricultural material on the first side of the first housing towards the second outlet at an increased rate compared to the agricultural material on the second side of the first housing.

In at least one example embodiment, the system includes a second housing configured to be coupled to the elevator. The second housing includes a second inlet configured to receive at least a portion of the agricultural material, a third chamber coupled to the second inlet, a third outlet coupled to the third chamber, a fourth chamber coupled to the third chamber, a second funnel portion between the third chamber and the fourth chamber, and a fourth outlet coupled to the fourth chamber. The fourth chamber includes a second metering conveyor. At least one sensor is coupled to an exterior of the second housing adjacent the third chamber. The at least one sensor is configured to detect a fill level of the second housing. A conduit is configured to be coupled between the second side of the elevator and the second inlet of the second housing. The conduit is configured to deliver at least a portion of the agricultural material from the second side of the elevator to the second inlet of the second housing.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For the purposes of clarity, various dimensions of the drawings may have been exaggerated.

DETAILED DESCRIPTION

Figure 1:
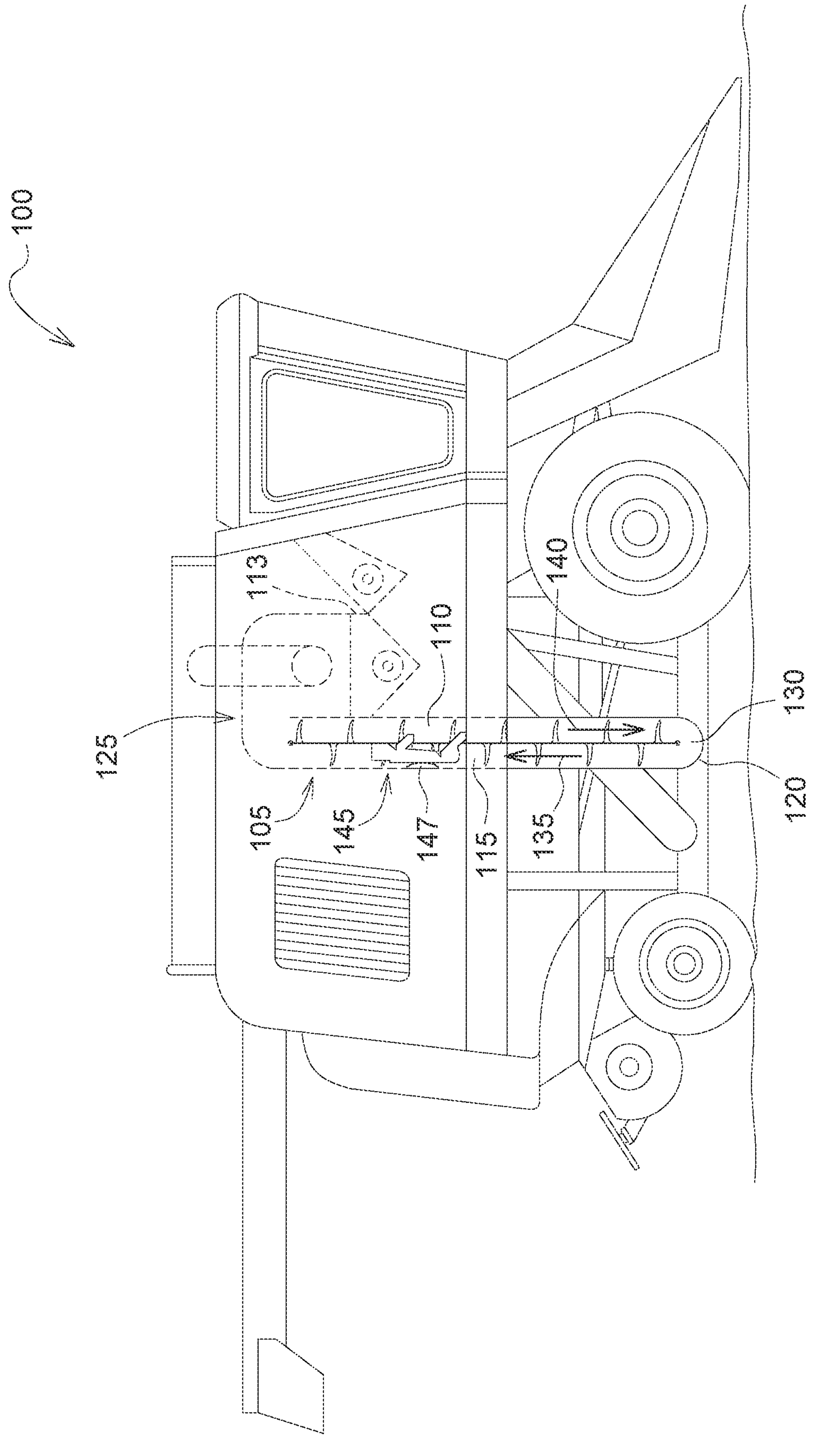
FIG. 1 is a side view of an agricultural machine in accordance with at least one example embodiment.

Agricultural harvesters may include at least one bypass coupled to a grain elevator for receiving a portion of the agricultural material and analyzing a grain quality of the agricultural material received. The bypass may not receive an accurate sample of agricultural material that is within the grain elevator if the bypass becomes too full. Additionally, the agricultural material within the bypass may separate based on material properties. For example, clean grain may separate from byproducts from a harvesting operation, such as material other than grain (MOG), while in the bypass. This separation of clean grain from MOG prevents sensors associated with the bypass from being presented with an accurate sample of the agricultural material within the bypass and skews any adjustments to the harvesting operation that might be made.

Example embodiments provide improved apparatuses, systems, and methods for presenting an accurate representation of agricultural material within a grain elevator of a harvester to a bypass including at least one sensor. For example, the bypass may include an overflow to prevent the bypass from becoming too full. The bypass may also direct the agricultural material within the bypass to the sensors such that the sensors are presented with an accurate sample representing the agricultural material within the grain elevator and the bypass.

Example embodiments also provide improved apparatuses, systems, and methods for moving the agricultural material though the bypass at a steady. For example, a rate of operation of a metering conveyor within the bypass may be controlled based on a fill level of the bypass and a type of the agricultural material moving through the bypass. The agricultural material may move steadily through the bypass such that overflow is prevented.

Some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed concurrently, simultaneously, contemporaneously, or in some cases be performed in reverse order.

It will be understood that when an element is referred to as being "connected" or "coupled" to another element, it may be directly connected or coupled to the other element or intervening elements may be present. As used herein the term "and/or" includes any and all combinations of one or more of the associated listed items.

Although terms of "first" or "second" may be used to explain various components (or parameters, values, etc.), the components (or parameters, values, etc.) are not limited to the terms. These terms should be used only to distinguish one component from another component. For example, a "first" component may be referred to as a "second" component, or similarly, and the "second" component may be referred to as the "first" component. Expressions such as "at least one of" when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a side view of an agricultural machine in accordance with at least one example embodiment.

In at least one example embodiment, an agricultural machine 100 includes an elevator 105, a chamber 113, and at least one bypass, such as a first bypass 145. The elevator 105 may include a first side 110 and a second side 115 extending from a bottom portion 120 to a top portion 125. The elevator 105 may also define a receptacle 130 adjacent the bottom portion 120 between the first side 110 and the second side 115 of the elevator 105. In at least one example embodiment, the receptacle 130 is configured to receive the agricultural material harvested during a harvesting operation of the agricultural machine 100.

In at least one example embodiment, the elevator 105 may include a plurality of paddles configured to move a first direction, indicated by arrow 135, on the second side 115 of the elevator 105 and a second direction, indicated by arrow 140, on the first side 110 of the elevator 105. For example, each of the paddles may be connected to a chain configured to rotate within the elevator 105. In at least one example embodiment, the plurality of paddles may be configured to deliver at least a portion of the agricultural material from the receptacle 130 to the chamber 113 and to the first bypass 145. For example, a portion of the agricultural material may be delivered to the first bypass 145 and a remaining agricultural material may be delivered to the chamber 113.

Figure 2A:
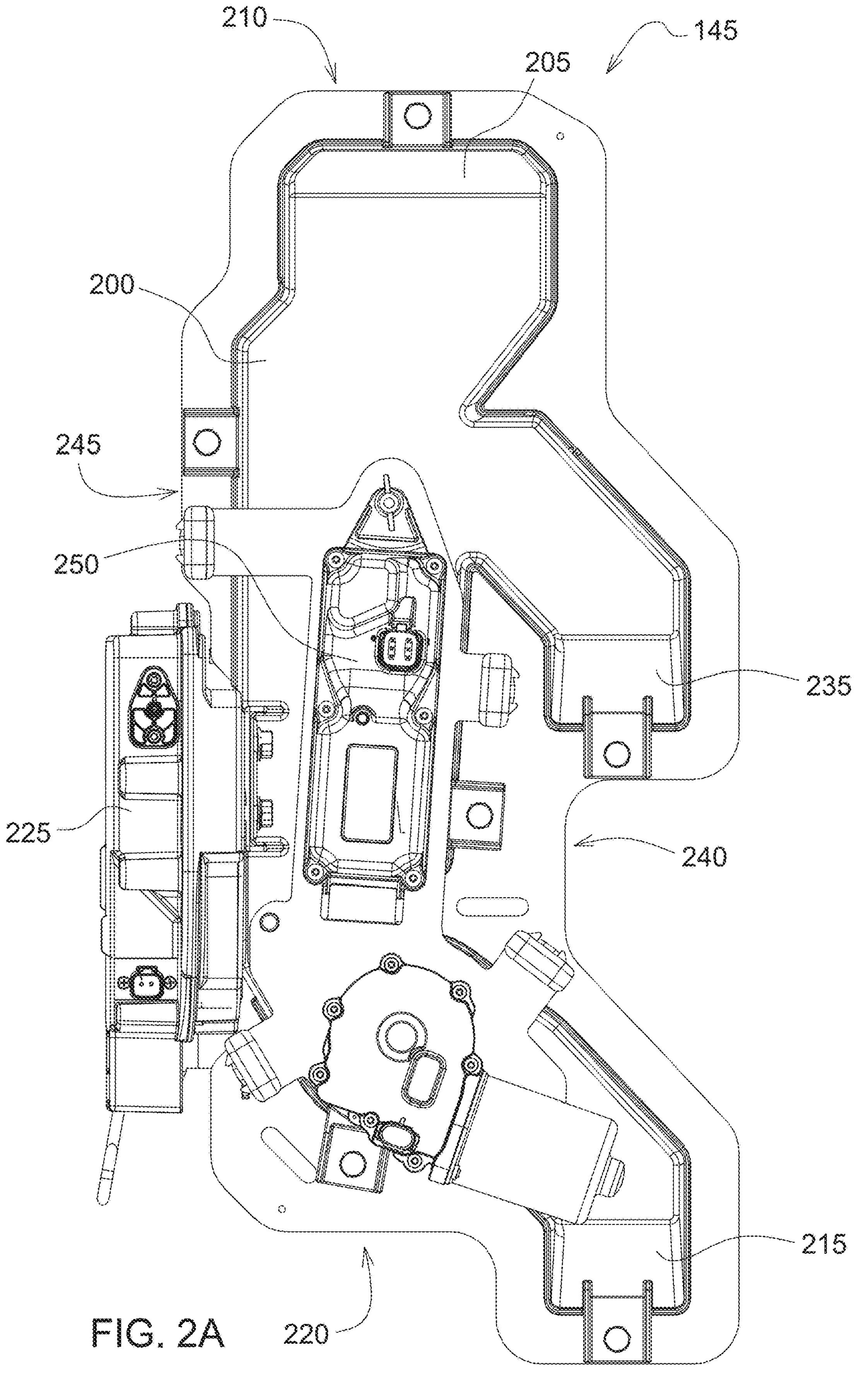
FIG. 2A is a side view of a first bypass for the agricultural machine of FIG. 1 according to at least one example embodiment.
Figure 2B:
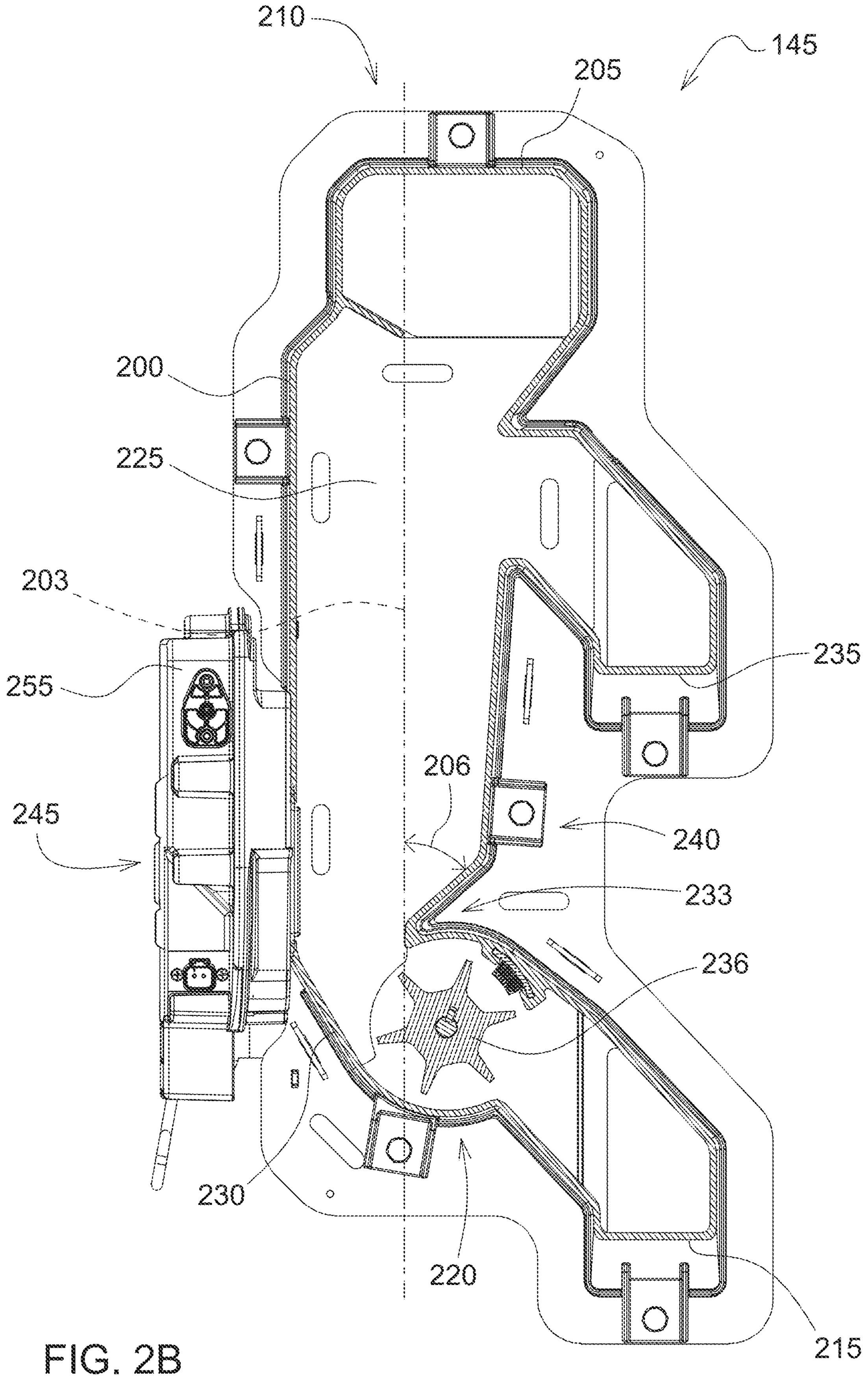
FIG. 2B is a side, cross-sectional view of the first bypass of FIG. 2A according to at least one example embodiment.

FIG. 2A is a side view of a first bypass for the agricultural machine of FIG. 1 according to at least one example embodiment. FIG. 2B is a side, cross-sectional view of the first bypass of FIG. 2A according to at least one example embodiment.

In at least one example embodiment, the first bypass 145 includes a housing 200. The housing may define an inlet 205, a first outlet 235, and a second outlet 215. The inlet 205 may be adjacent a first end 210 of the first bypass 145 and the second outlet 215 may be adjacent a second end 220 of the first bypass 145 opposite the first end 210. The inlet 205 may be configured to receive at least a portion of the agricultural material from the elevator 105. For example, the elevator 105 may include an opening adjacent the inlet 205 of the first bypass 145. At least a portion of the agricultural material moving through the elevator 105 may be configured to enter the inlet 205 through the opening in the elevator 105.

In at least one example embodiment, the housing 200 of the first bypass 145 includes a first chamber, such as a sensing chamber 225, adjacent the first end 210 and a second chamber, such as a metering chamber 230, adjacent the second end 220. For example, the sensing chamber 225 may be upstream or above the metering chamber 230. In at least one example embodiment, the sensing chamber 225 may be coupled to the inlet 205 and the metering chamber may be coupled to the second outlet 215. The sensing chamber 225 and the metering chamber 230 may also be coupled within the first bypass 145. In at least one example embodiment, the metering chamber 230 includes a metering conveyor 236 configured to move the agricultural material from the metering chamber 230 toward the second outlet 215. In other example embodiments, the metering conveyor 236 may comprise a metering wheel, an auger, or a roller.

In at least one example embodiment, the first bypass 145 includes a funnel portion 233. The funnel portion 233 may be between the sensing chamber 225 and the metering chamber 230. In at least one example embodiment, the funnel portion 233 includes at least a portion of a wall of the housing 200 extending over and along at least a portion of the metering conveyor 236. For example, the wall of the housing 200 may extend from a first side 240 of the housing 200 towards a second side 245 of the housing 200. In another example embodiment, a width of at least a portion of the housing 200 may taper or decrease from the sensing chamber 225 towards the metering chamber 230 to form the funnel portion 233. For example, the funnel portion 233 may taper between the sensing chamber 225 and the metering chamber 230.

In at least one example embodiment, the housing 200 and the funnel portion 233 of the first bypass 145 are configured to sort the agricultural material received through the inlet 205 by size and/or density. The first bypass 145, including the funnel portion 233, may cause the agricultural material to fill the sensing chamber 225 and the metering chamber 230 at an angle, forming a hill within the sensing chamber 225. For example, an angle 206 formed between the funnel portion 233 and a vertical axis 203 extending through the first bypass from the first end 210 to the second end 220 may be between about 50° and about 55°. In at least one example embodiment, the housing 200 and/or the funnel portion 233 of the first bypass 145 are configured to separate the agricultural material into a first flow and a second flow. The first flow may have a first density and the second flow may have a second density. In at least one example embodiment, the first density is greater than the second density. In at least one example embodiment, the portion of agricultural material having the higher or increased density, such as the first flow, may collect over the funnel portion 233 of the housing 200. For example, the funnel portion 233 and/or the housing 200 may direct the first flow of agricultural material along the first side 240 of the housing 200. Another portion of the agricultural material having a lower or reduced density, such as the second flow, may be configured to collect adjacent the second side 245 of the housing 200. For example, the funnel portion 233 and/or the housing 200 may direct the second flow of the agricultural material along the second side 245 of the housing 200. Additionally or alternatively, the portion of agricultural material having the higher or increased density, such as the first flow, may have a smaller particle size compared to the portion of the agricultural material having a lower or reduced density in some embodiments, such as the second flow. In at least one example embodiment, the portion of the agricultural material having the lower or reduced density and adjacent the second side 245 of the housing 200, such as the second flow, may move from the sensing chamber 225 to the metering chamber 230 at a higher or increased rate compared to the agricultural material adjacent the first side 240 of the housing 200, such as the first flow. Accordingly, the portion of the agricultural material having the increased density and/or smaller particle size collects over the funnel portion 233 so that the portion of the agricultural material having the reduced density and/or larger particle size is sorted adjacent to the second side 245 of the housing 200 and flows into the metering chamber 230 at an increased rate compared to the portion of the agricultural material having the increased density and/or smaller particle that collects over the funnel portion 233 adjacent the first side 240 of the housing 200.

In at least one example embodiment, at least one sensor may be coupled to the housing 200. The funnel portion 233 causes the agricultural material to be sorted by size and/or density, which allows the agricultural material to be presented to the at least one sensor in a measurable state. For example, a first sensor 250 may be coupled to the first side 240 of the housing 200, as shown in FIG. 2A, and a second sensor 255 may be coupled to the second side 245 of the housing 200 as shown in FIG. 2B. In other example embodiments, the first sensor 150 may be coupled on a side of the housing 200 perpendicular to the first side 240, such as shown in FIG. 2A. The first sensor 250 and the second sensor 255 may comprise one or more of a moisture sensor, a near-infrared (NIR) sensor, a temperature sensor, a capacitive sensor, and a proximity sensor. In at least one example embodiment, the second sensor 255 comprises a camera. The camera may be configured to measure the grain quality within the sensing chamber 225 and/or the metering chamber 230 of the first bypass 145. For example, the camera may be configured to determine whether the agricultural material received by the first bypass 145 includes clean grain and/or MOG which provides a representation of the agricultural material being harvested within the elevator 105. If the camera detects that most of the agricultural material being harvested is MOG, this may indicate that adjustments to the harvesting operation need to be made.

In at least one example embodiment, the agricultural material is configured to flow from the inlet 205 through the sensing chamber 225 towards the funnel portion 233. The funnel portion 233 may cause the agricultural material to be presented to the first sensor 250 and the second sensor 255 in a measurable state based on the sorting discussed above. The funnel portion 233 then directs the agricultural material to the metering conveyor 236 within the metering chamber 230. The metering conveyor 236 pushes the agricultural material toward the second outlet 215 where the agricultural material is then dropped into the first side 110 of the elevator 105. In at least one example embodiment, the metering conveyor 236 rotates at a constant speed. In other example embodiment, the metering conveyor 236 may rotate at a variable speed.

In at least one example embodiment, the first outlet 235 is adjacent the first end 210 of the first bypass 145 and may be coupled to the sensing chamber 225. In at least one example embodiment, the first outlet 235 may be configured to allow agricultural material to flow out of the sensing chamber 225 and into the first side 110 of the elevator 105 such that the agricultural material returns to the receptacle 130. For example, when the agricultural material is flowing at a faster rate than the metering conveyor 236 can empty the metering chamber 230 and the sensing chamber 225, at least a portion of the agricultural material may flow out of the housing 200 through the first outlet 235 without passing fully through the sensing chamber 225. In such embodiments, the first outlet 235 prevents (and/or reduces the likelihood of) the agricultural material from overflowing within the housing 200 of the first bypass 145, such as accumulating and overflowing through the inlet 205. In at least one other example embodiment, the first outlet 235 may be coupled to the second outlet 215. For example, the agricultural material may exit through the first outlet 235, travel through a passageway or conduit coupling the first outlet 235 and the second outlet 215, and exit through the second outlet 215 into the first side 110 of the elevator 105 and to the receptacle 130.

Figure 3:
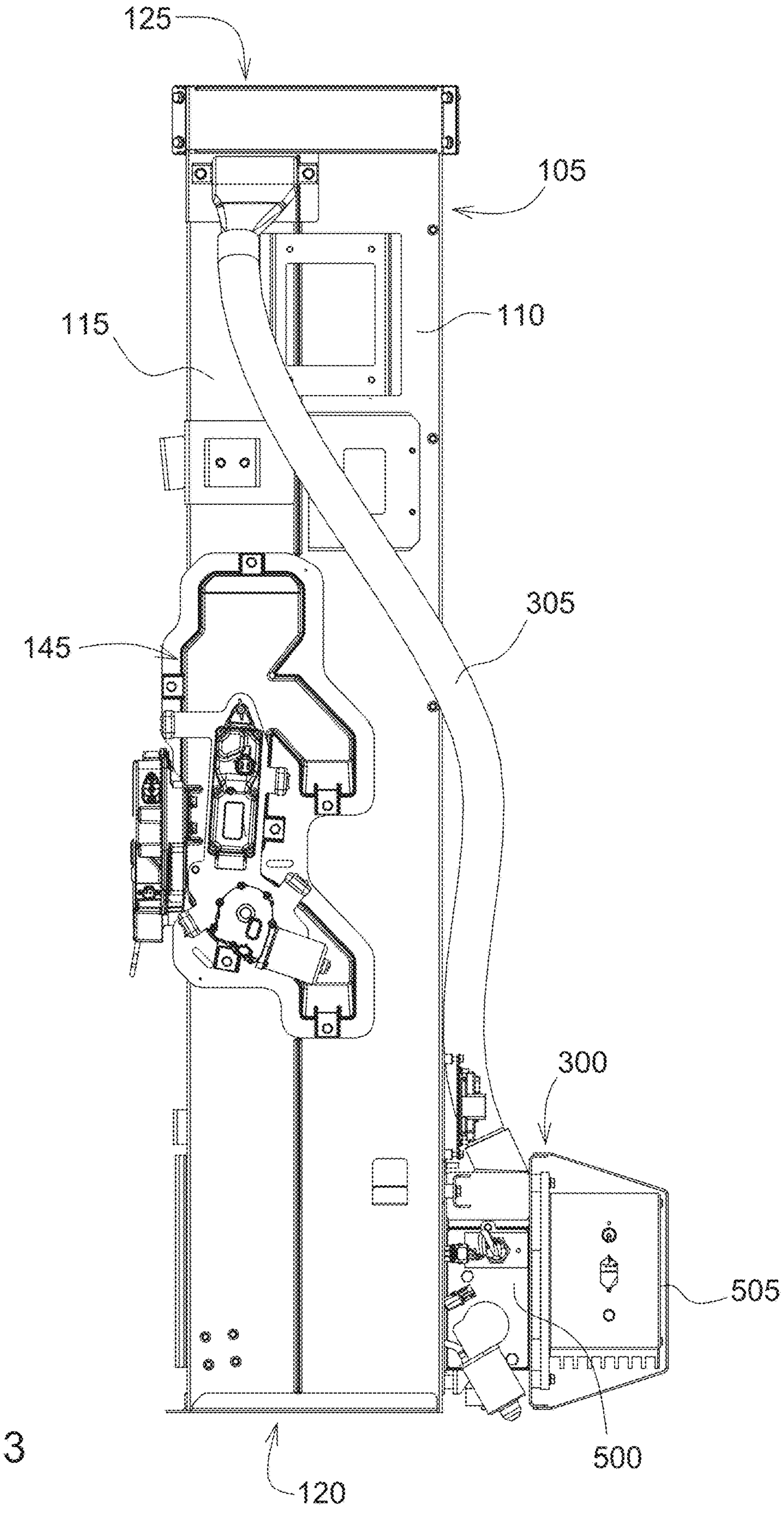
FIG. 3 is a side view of an elevator of the agricultural machine of FIG. 1 including the first bypass of FIG. 2A and a second bypass according to at least one example embodiment.

FIG. 3 is a side view of an elevator of the agricultural machine of FIG. 1 including the first bypass of FIG. 2A and a second bypass according to at least one example embodiment.

In at least one example embodiment, the agricultural machine 100 may include a second bypass 300 coupled to or mounted on the elevator 105. For example, the second bypass 300 may be coupled to the first side 110 of the elevator 105 opposite the first bypass 145. In at least one example embodiment, the second bypass 300 may be positioned below or downstream of the first bypass 145. For example, the second bypass 300 may be adjacent the bottom portion 120 of the elevator 105. In other example embodiments, the second bypass 300 may be positioned above or upstream of the first bypass 145 or may be aligned with the first bypass 145 on the elevator 105.

In at least one example embodiment, the second bypass 300 includes a housing 500 and at least one sensor, such as a first sensor 505, coupled to the housing 500. The housing 500 of the second bypass 300 is configured to receive at least a portion of the agricultural material from the second side 115 of the elevator 105. For example, a hose, conduit, or tube, such as a conduit 305, may be coupled between an opening in the second side 115 of the elevator and the second bypass 300 and configured to guide at least a portion of the agricultural material from the second side 115 of the elevator 105 to the housing 500 of the second bypass 300.

Figure 4A:
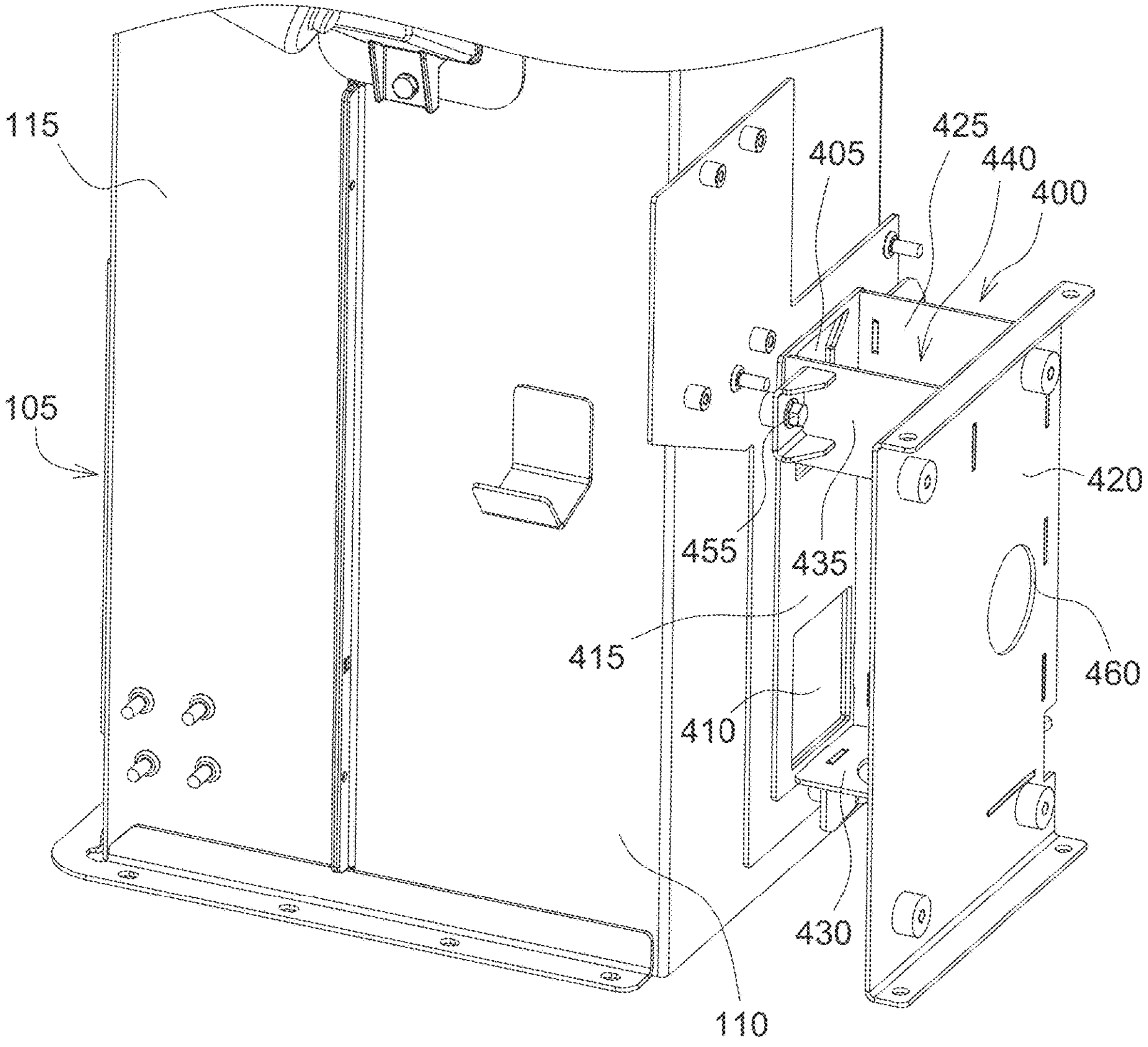
FIG. 4A is a side, perspective view of an attachment device for the second bypass of FIG. 3 according to at least one example embodiment.
Figure 4B:
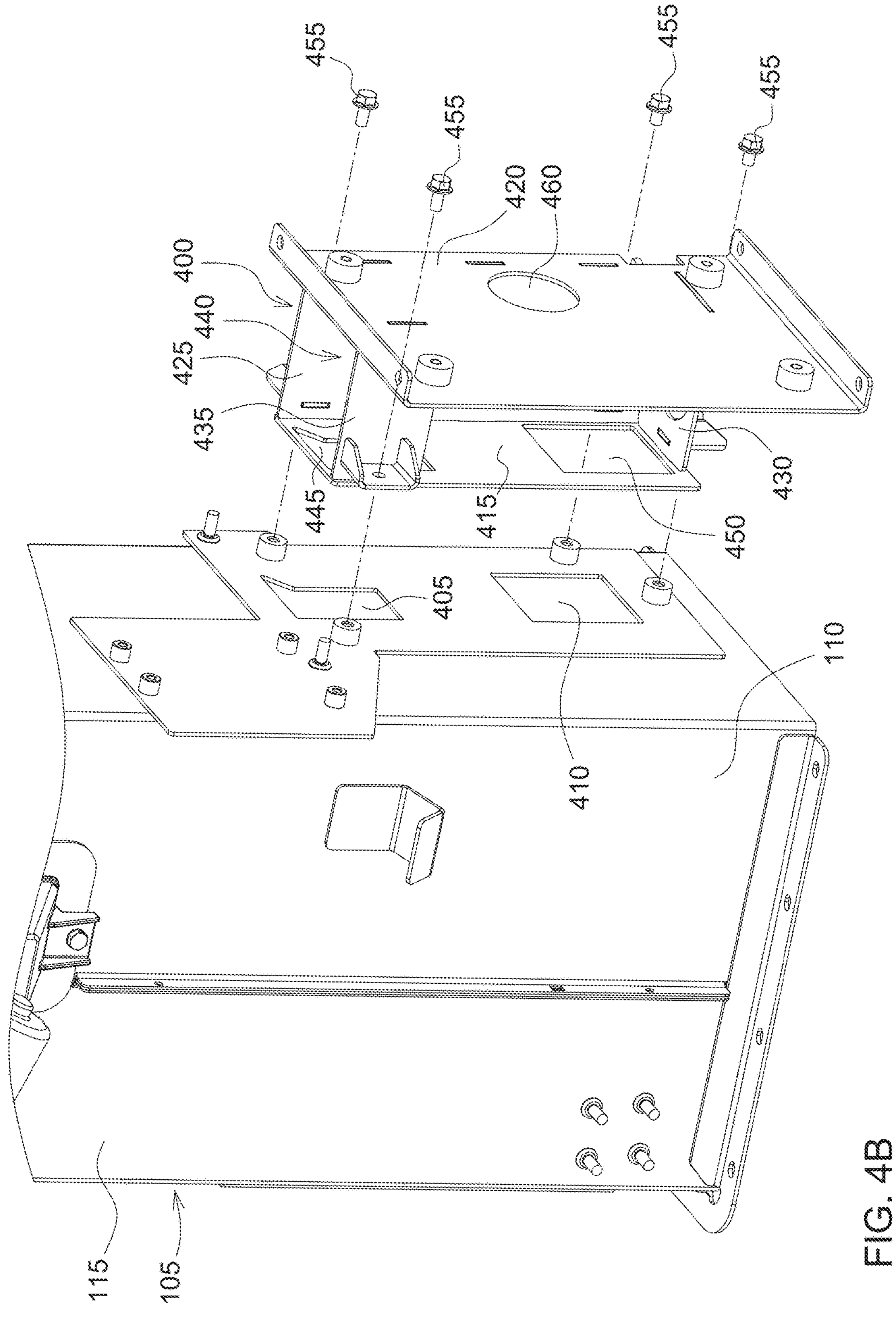
FIG. 4B is an exploded view of the attachment device of FIG. 4A according to at least one example embodiment.

FIG. 4A is a side, perspective view of an attachment device for the second bypass of FIG. 3 according to at least one example embodiment. FIG. 4B is an exploded view of the attachment device of FIG. 4A according to at least one example embodiment.

In at least one example embodiment, the second bypass 300 may be coupled to the elevator 105 by an attachment device 400. The attachment device 400 may be configured to be coupled to an exterior portion of the first side 110 of the elevator 105. For example, the attachment device 400 may be coupled and secured to the elevator 105 by a plurality of bolts 455. In at least one example embodiment, the attachment device 400 includes a first wall 415, a second wall 420, a third wall 425, and a bracket 435. The first wall 415 is opposite the second wall 420 such that the first wall 415 is parallel to the second wall 420. The third wall 425 is opposite the bracket 435 such that the third wall 425 is parallel to the bracket 435. Additionally, the first wall 415 and the second wall 420 are perpendicular to the third wall 425 and the bracket 435. In at least one example embodiment, the third wall 425 is coupled to edges of the first wall 415 and the second wall 420. In at least one example embodiment, a width of the first wall 415 is less than a width of the second wall 420. In such embodiments, the bracket 435 may be coupled to an edge of the first wall opposite the third wall 425 and coupled to a middle portion of the second wall 420. In other example embodiments, the width of the first wall 415 and the width of the second wall 420 may be the same.

In at least one example embodiment a height of each of the first wall 415, the second wall, 420, and the third wall 425 may be the same. A height of the bracket 435 may be less than the height of each of the first wall 415, the second wall, 420, and the third wall 425. For example, the bracket 435 may be coupled to a top portion of the first wall 415 and the second wall 420.

In at least one example embodiment, the attachment device 400 includes a base wall 430. The base wall 430 may by perpendicular to the first wall 415, the second wall 420, the third wall 425, and the bracket 435. The base wall 430 may be coupled to bottom edges of the first wall 415, the second wall 420, and/or the third wall 425 and form a base or bottom portion of the attachment device 400.

In at least one example embodiment, the first wall 415, the second wall 420, the third wall, 425, the bracket 435, and the base wall 430 may at least partially define a receptacle 440. The receptacle 440 may be configured to receive the housing 500 of the second bypass 300, as shown in FIGS. 5A-5D. In at least one example embodiment, the first sensor 505 of the second bypass 300 may be configured to be coupled to the second wall 420 opposite the housing 500.

In at least one example embodiment, the first side 110 of the elevator 105 includes a first opening 405 and a second opening 410. The first wall 415 may define a third opening 445 configured to be coupled to the first opening 405 and a fourth opening 450 configured to be coupled to the second opening 410. The first opening 405, the second opening 410, the third opening 445, and the fourth opening 450 are configured to couple the second bypass 300 to an interior portion of the elevator 105, as will be described below with respect to FIGS. 5A-5D.

In at least one example embodiment, the second wall 420 defines a fifth opening 460. The fifth opening 460 is configured to allow the first sensor 505 to have a view within at least a portion of the housing 500 of the second bypass 300. For example, the fifth opening 460 may correspond with an opening or transparent window of the housing 500, as will be discussed below with respect to FIG. 5D.

Figure 5A:
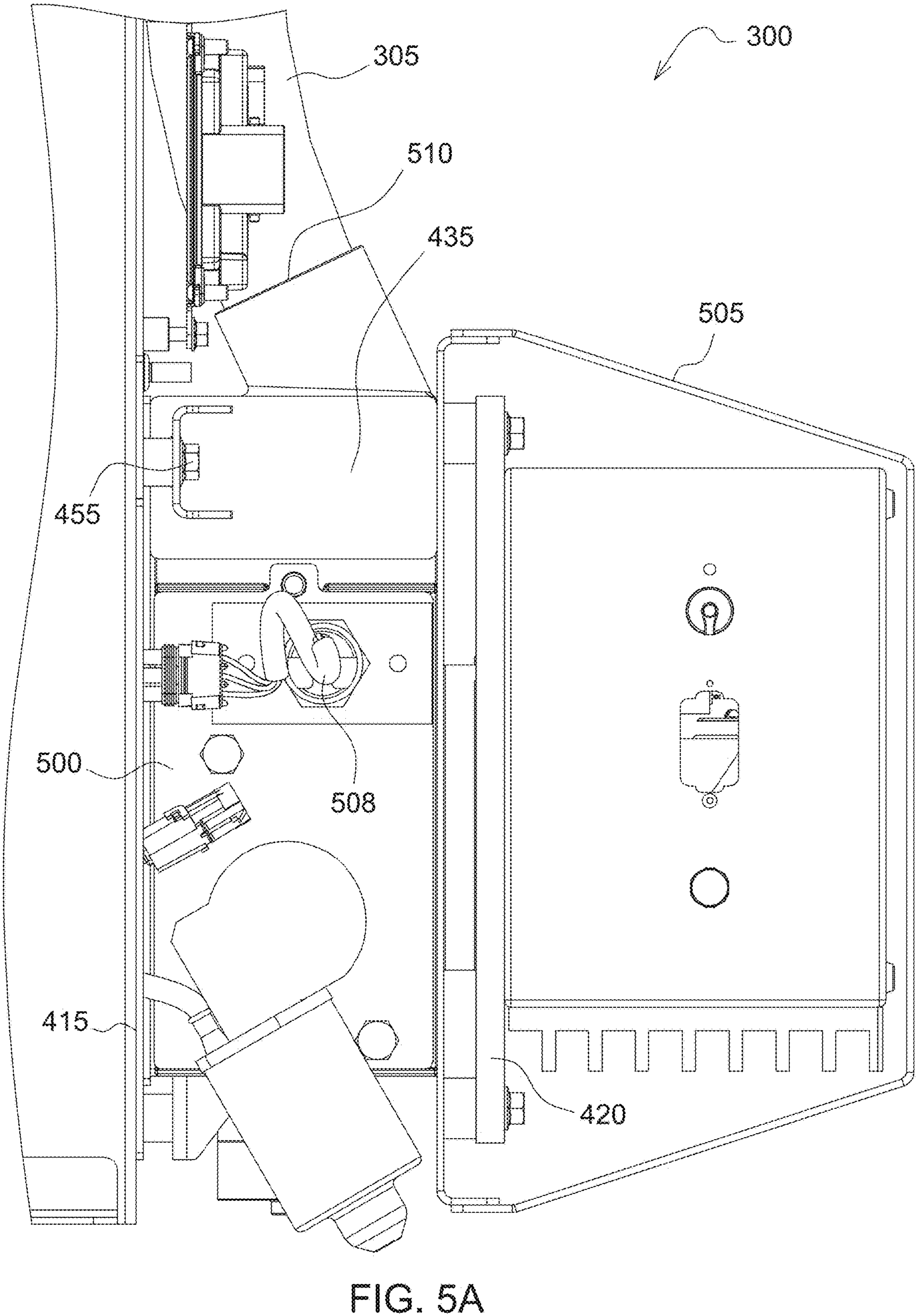
FIG. 5A is a side view of the second bypass of FIG. 3 according to at least one example embodiment.
Figure 5B:
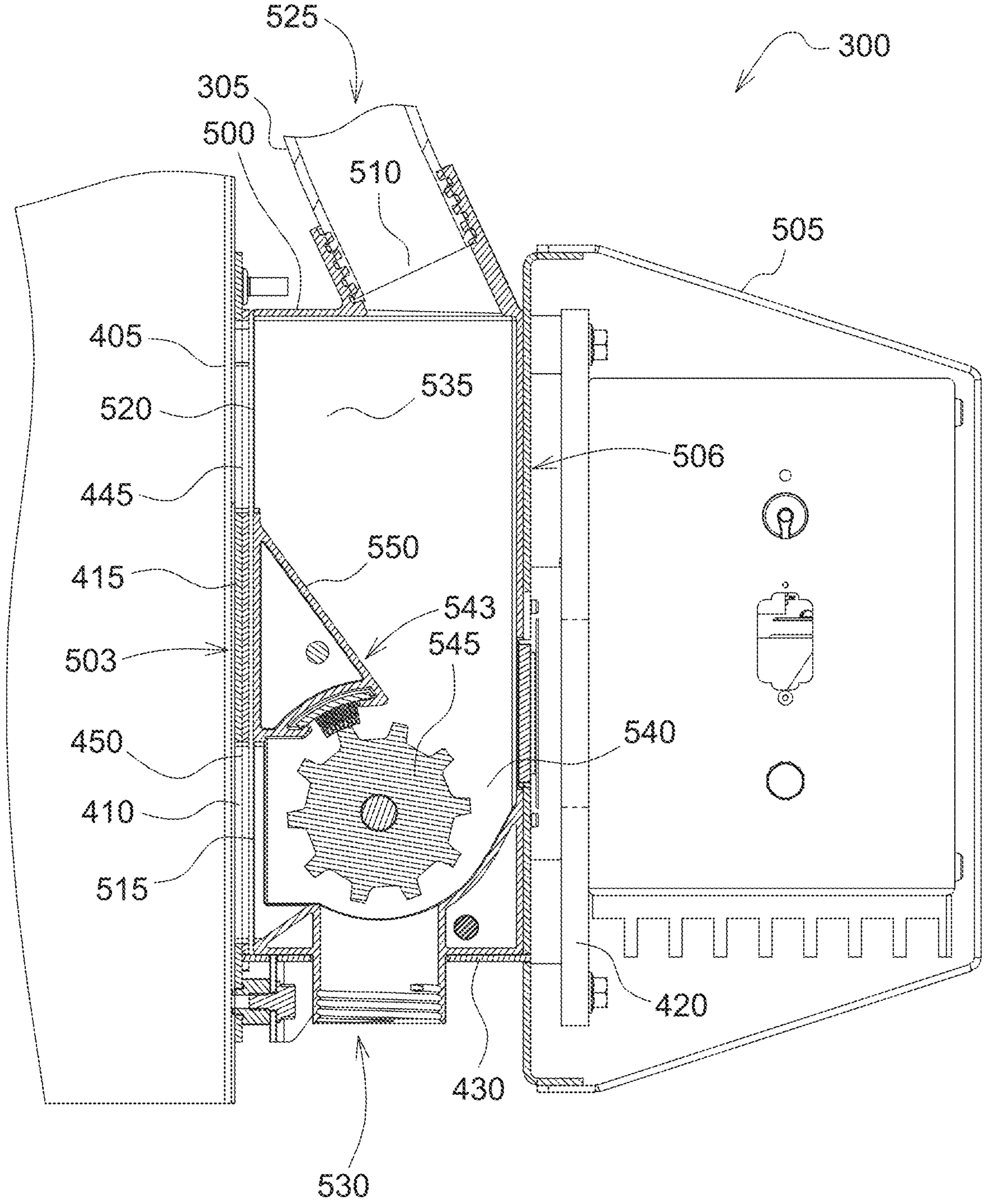
FIG. 5B is a cross-sectional view of the second bypass of FIG. 5A according to at least one example embodiment.
Figure 5C:
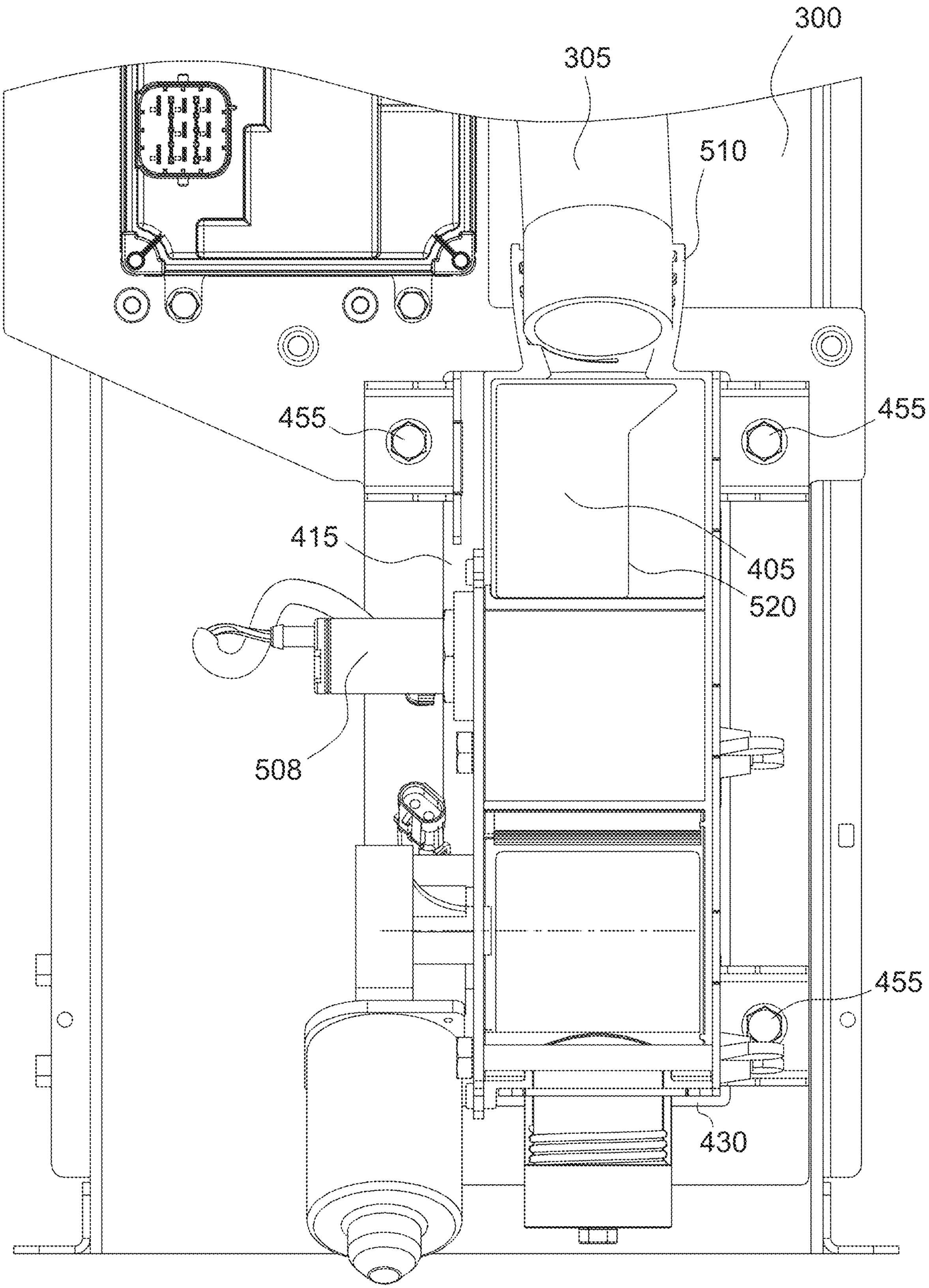
FIG. 5C is a front, cross-sectional view of an inlet, a first outlet, and a second outlet of the bypass of FIG. 5A according to at least one example embodiment.
Figure 5D:
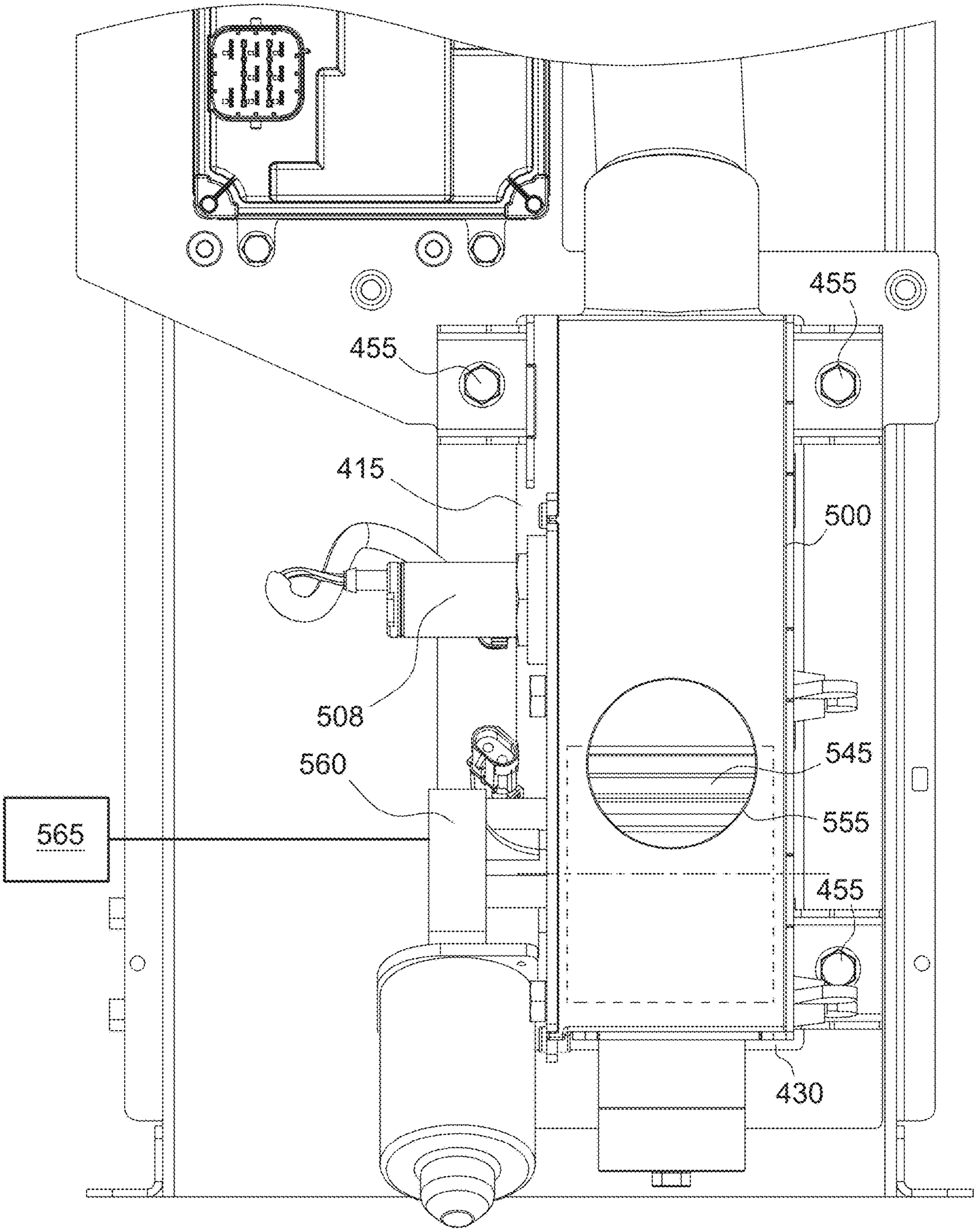
FIG. 5D is a front, cross-sectional view of a portion of the second bypass of FIG. 5A according to at least one example embodiment.

FIG. 5A is a side view of the second bypass of FIG. 3 according to at least one example embodiment. FIG. 5B is a cross-sectional view of the second bypass of FIG. 5A according to at least one example embodiment. FIG. 5C is a front, cross-sectional view of an inlet, a first outlet, and a second outlet of the bypass of FIG. 5A according to at least one example embodiment. FIG. 5D is a front, cross-sectional view of a portion of the second bypass of FIG. 5A according to at least one example embodiment.

In at least one example embodiment, the second bypass 300 includes the housing 500 and at least one sensor coupled to the housing 500. For example, the first sensor 505 and a second sensor 508 may be coupled the housing 500. In at least one example embodiment, the housing 500 defines an inlet 510, a first outlet, such as an overflow outlet 520, and a second outlet, such as a return outlet 515. The inlet 510 may be adjacent a first end 525 of the housing 500 and configured to receive at least a portion of the agricultural material from the elevator 105 through the conduit 305. In at least one example embodiment, the return outlet 515 and the overflow outlet 520 are disposed in a wall of the housing 500 on the first side 503.

In at least one example embodiment, the housing 500 of the second bypass 300 includes a first chamber, such as a sensing chamber 535, adjacent the first end 525 and a second chamber, such as a metering chamber 540, adjacent a second end 530 opposite the first end 525. For example, the sensing chamber 535 may be above or upstream of the metering chamber 540. The sensing chamber 535 may be coupled to the inlet 510 and the overflow outlet 520. The metering chamber 540 may be coupled to the return outlet 515. The sensing chamber 535 and the metering chamber 540 may also be coupled within the housing 500 of the second bypass 300. In at least one example embodiment, the metering chamber 540 includes a metering conveyor 545. The metering conveyor 545 may comprise a metering wheel, an auger, or a roller in some example embodiments.

In at least one example embodiment, the second bypass 300 includes a funnel portion 543. The funnel portion 543 may be between the sensing chamber 535 and the metering chamber 540. In at least one example embodiment, the funnel portion 543 includes a wall 550 extending from an interior of the housing 500 from a first side 503 towards a second side 506. For example, the wall 550 may extend from the first side 503 and over at least a portion of the metering conveyor 545. In at least one example embodiment, the wall 550 comprises a substantially triangular shape in cross-section. In another example embodiment, a width of at least a portion of the housing 500 may taper or decrease from the sensing chamber 535 towards the metering chamber 540. For example, the funnel portion 543 may taper between the sensing chamber 535 and the metering chamber 540.

In at least one example embodiment, the housing 500 and the funnel portion 543 of the second bypass 300 are configured to sort the agricultural material received through the inlet 510 by size and/or density, similar to the first bypass 145 discussed above with respect to FIGS. 2A-2B. For example, the housing 500 and/or the funnel portion 543 may be configured to separate the agricultural material in a first flow and a second flow. The first flow may have a first density and the second flow may have a second density. In at least one example embodiment, the first density is greater than the second density. In at least one example embodiment, the portion of agricultural material having a higher or increased density, such as the first flow, may collect over the funnel portion 543 of the housing 500. For example, the funnel portion 543 and/or the housing 500 may direct the first flow of the agricultural material along the first side 503 of the housing 500. Another portion of the agricultural material having a lower or reduced density, such as the second flow, may be configured to collect adjacent the second side 506 of the housing 500. For example, the funnel portion 543 and/or the housing 500 may direct the second flow of the agricultural material along the second side 506 of the housing 500. In such embodiments, the second flow of the agricultural material having the lower or reduced density and adjacent the second side 506 of the housing 500 may move from the sensing chamber 535 to the metering chamber 540 at a higher or increased rate than the first flow, such as the agricultural material adjacent the first side 503 of the housing 500.

In at least one example embodiment, the agricultural material is configured to flow from the inlet 510 through the sensing chamber 535 to the funnel portion 543. The funnel portion 543 then directs the agricultural material to the metering conveyor 545 within the metering chamber 540. The metering conveyor 545 pushes the agricultural material toward the return outlet 515 and through the second opening 410 where the agricultural material is then deposited into the first side 110 of the elevator 105. In at least one example embodiment, the metering conveyor 236 rotates at a constant speed. In other example embodiment, the metering conveyor 236 may rotate at a variable speed, as will be discussed below with respect to FIG. 6.

In at least one example embodiment, the overflow outlet 520 may be coupled to the first opening 405 in the elevator 105 and configured to allow agricultural material to flow out of the sensing chamber 535 and into the first side 110 of the elevator 105 such that the agricultural material may return to the receptacle 130. For example, when the agricultural material is flowing at a faster rate than the metering conveyor 545 can empty the metering chamber 540 and the sensing chamber 535, at least a portion of the agricultural material may flow out of the housing 500 through the overflow outlet 520 without passing fully through the sensing chamber 535. In such embodiments, the overflow outlet 520 prevents the agricultural material from overflowing within the housing 500 of the second bypass 300, such as accumulating and overflowing through the inlet 510.

In at least one example embodiment, the first sensor 505 and the second sensor 508 may each comprise a camera, a moisture sensor, a near-infrared (NIR) sensor, a temperature sensor, a capacitive sensor, and a proximity sensor. For example, the first sensor 505 may be a camera similar to the second sensor 255 discussed above with respect to FIGS. 2A-2B. In at least one example embodiment, the side of the housing 500 adjacent the first sensor 505, such as the second side 506, may define a window 555. The window 555 may allow the sensor to view inside at least a portion of the interior of the housing 500. For example, the first sensor 505 may be a camera configured to measure the grain quality within the sensing chamber 535 and/or the metering chamber 540 of the second bypass 300. In such embodiments, the first sensor 505 may be configured to determine whether the agricultural material received by the second bypass 300 includes clean grain and/or MOG, which provides a representation of the agricultural material being harvested within the elevator 105. If the first sensor 505 detects that most of the agricultural material being harvested is MOG, then this may indicate that adjustments to the harvesting operation need to be made.

In at least one example embodiment, the second sensor 508 may comprise a proximity sensor configured to detect a fill level of the agricultural material within the housing 500. For example, the second sensor 508 may be configured to generate a signal indicative of a distance between the second sensor 508 and the agricultural material within the housing 500. If the agricultural material within the housing 500 is within a threshold distance of the second sensor 508, then a controller, such as a controller 565, may receive the signal and determine that the second sensor 508 is covered or obstructed. In at least one example embodiment, the controller 565 may be communicatively coupled to a motor 560 of the metering conveyor 545, as shown in FIG. 5D, and may be configured to control a rate of operation of the metering conveyor 545 based on the fill level detected by the second sensor 508, as will be discussed in more detail with respect to FIG. 6 below. Examples of the rate of operation of the metering conveyor 545 include a speed at which the metering conveyor 545 moves, a velocity at which the metering conveyor 545 moves, a frequency at which the metering conveyor 545 moves, and combinations thereof. Such examples of the rate of operation of the metering conveyor 545 are not exhaustive. The speed at which the metering conveyor moves may also include a linear speed, rotational speed, or combinations thereof. In at least one example embodiment, the controller 565 may control the rate of operation, such as the rotational speed, of the metering conveyor 545 to keep the agricultural material within the housing 500 moving at a steady rate from the inlet 510, through the sensing chamber 535 and the metering chamber 540, and out the return outlet 515 without overflowing through the overflow outlet 520. The controller 565 may also be configured to control the rotational speed of the metering conveyor 545 based on the type of agricultural material within the housing 500. For example, the controller 565 may increase or decrease the rotational speed of the metering conveyor 545 based on the size, density, and/or type of agricultural material within the housing 500.

Figure 6A:
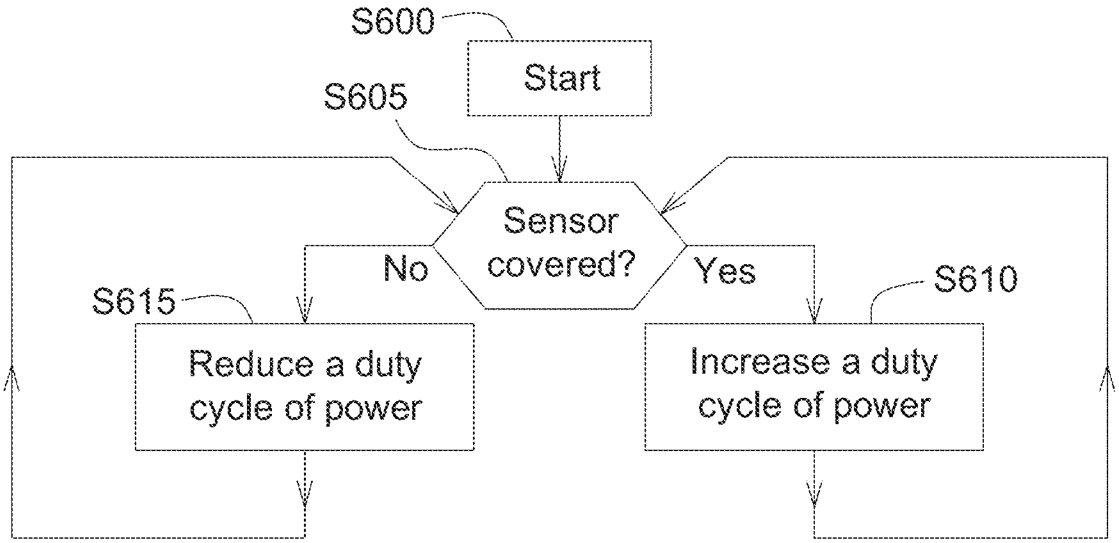
FIG. 6A is a flow chart of a method for controlling a rotational speed of a metering conveyor of a second bypass according to at least one example embodiment.
Figure 6B:
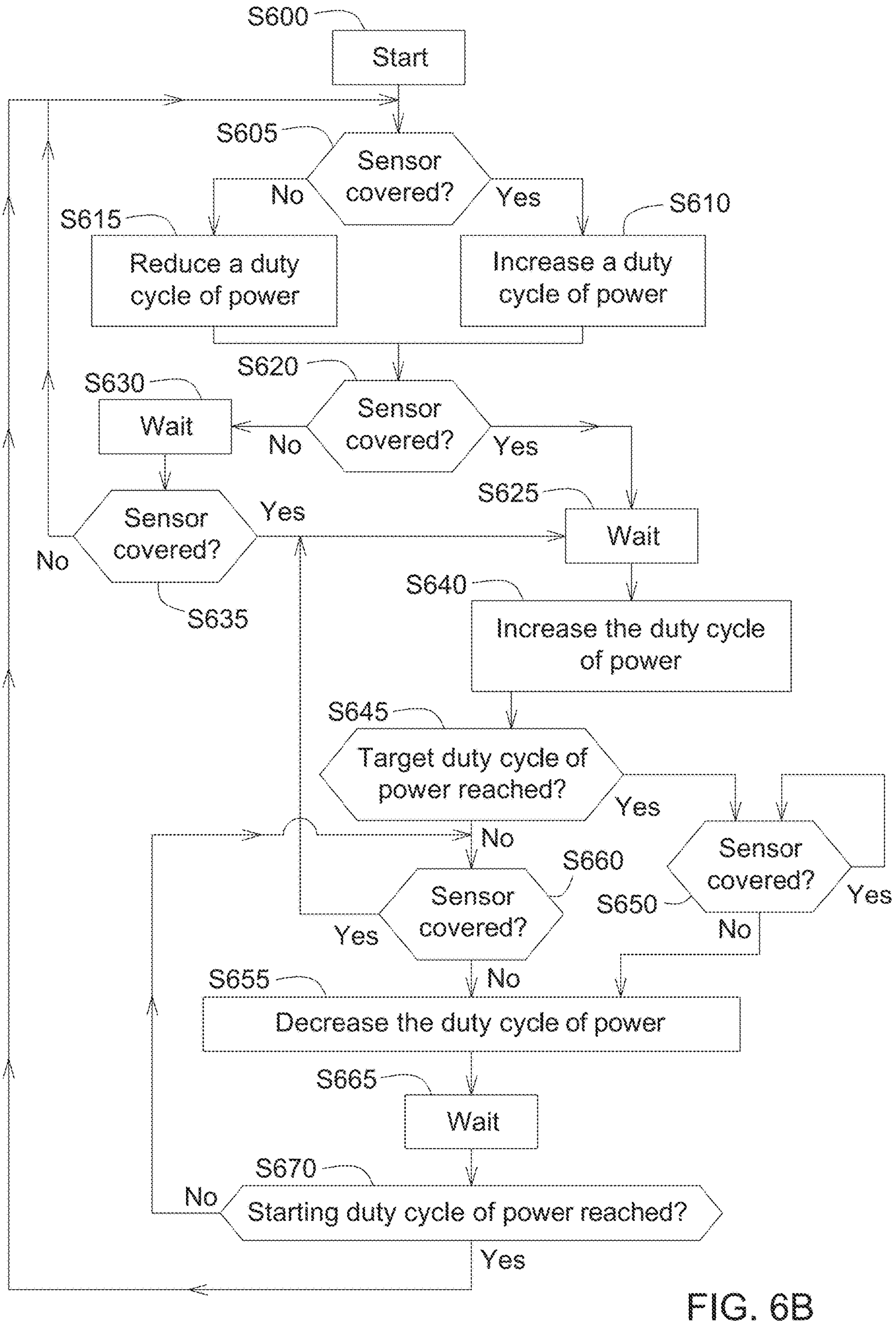
FIG. 6B is a flow chart including further details of the method of controlling the rotational speed of the metering conveyor of the second bypass of FIG. 6A according to at least one example embodiment.

FIG. 6A is a flow chart of a method for controlling a rotational speed of a metering conveyor of a second bypass according to at least one example embodiment. FIG. 6B is a flow chart including further details of the method of controlling the rotational speed of the metering conveyor of the second bypass of FIG. 6A according to at least one example embodiment. In at least one example embodiment, the methods of FIGS. 6A-6B may be used for the second bypass of FIG. 3.

In at least one example embodiment, the controller 565 is configured to perform a motor control method to control the rotational speed of the metering conveyor 545 based on the fill level of the agricultural material within the housing 500 of the second bypass 300. For example, the motor control method may be configured to increase and/or decrease the rotational speed of the metering conveyor 545 in order to maintain a steady flow of agricultural material through the second bypass 300. For example, pulse-width modulation (PWM) may be used to control the supply of power and/or voltage to the metering conveyor. In at least one example embodiment, the duty cycle of power refers to pulse width modulating a voltage signal to generate a desired power. In at least one example embodiment, the speed of the metering conveyor 545 may be increased as a flow or mass of agricultural material through the second bypass increases and/or the speed of the metering conveyor 545 may be decreased as the flow or mass of agricultural material through the second bypass decreases.

In at least one example embodiment, the motor control method begins at S600. Beginning the method at S600 may include beginning a harvesting operation, determining that a separator of the harvesting machine is engaged, and/or determining whether the second sensor 508 is uncovered or unobstructed by the agricultural material.

In at least one example embodiment, the method includes determining whether the second sensor 508 is covered or obstructed by agricultural material at S605. If the second sensor 508 is at least partially covered with agricultural material at S605, such that the housing of the second bypass 300 is at least partially filled with agricultural material, then a duty cycle of power is applied, supplied, or increased to the metering conveyor 545 at S610. For example, the controller 565 may supply or increase the duty cycle of power to the motor 560 to increase the rotational speed of the metering conveyor 545. The duty cycle of power initially supplied to the metering conveyor 545 at S610 may be a starting value at 610. For example, the duty cycle of power may be increased at S610 such that the rotational speed of the metering conveyor 545 is increased to a starting speed. In at least one example embodiment, the duty cycle of power supplied to the metering conveyor 545 is based on the type of agricultural material being harvested. For example, the duty cycle of power supplied to the metering conveyor 545 may be between about 30% to about 60% when harvesting canola, about 30% to about 90% when harvesting wheat, and about 70% to about 100% when harvesting corn. After the duty cycle of power is increased at S610, the method proceeds to S620.

If the second sensor 508 is not covered at S605, the duty cycle of power supplied to the metering conveyor 545 is reduced, if necessary, at S615. For example, the duty cycle of power suppled to the metering conveyor 545 may be reduced such that the rotational speed of the metering conveyor is reduced. In at least one example embodiment, the duty cycle of power may be set to 0% at S615 such that little to no power is supplied to the metering conveyor 545. After supplying or increasing the duty cycle of power at S610 or reducing the duty cycle of power at S615, the method may return to S605 to continue determining whether the second sensor 508 is covered or obstructed by agricultural material.

With reference to FIG. 6B, the method of FIG. 6A may proceed to S620 to determine whether the second sensor 508 is covered a second time. If the second sensor 508 is not covered at S620, then a wait time is increased at S630. In at least one example embodiment, determining that the second sensor 508 is not covered at S620 could indicate an error, such as a low flow of agricultural material through the second bypass 300 and/or a blockage of the agricultural material within the elevator 105. After the wait time is increased at S630, the method includes determining whether the second sensor 508 is covered at a third time at S635. If the second sensor 508 is not covered at S635, then the method returns to S605. If the second sensor 508 is at least partially covered at S635, the method continues to S625 where the wait time is increased.

Returning to S620, if the second sensor 508 is covered at the second time, the wait time is increased at S625 and the duty cycle of power supplied to the metering conveyor 545 is increased at S640. For example, the rotational speed of the metering conveyor 545 may be increased at S640. In at least one example embodiment, the method includes determining whether the duty cycle of power supplied to and/or the rotational speed of the metering conveyor 545 has reached a target value, such as a target duty cycle of power or a target speed, at S645. If the target value has not been reached at S645, the method proceeds to S660. At S660, the method includes determining whether the second sensor 508 is covered. If the second sensor 508 is covered at S660, then the wait time of the system is increased at S625, and the duty cycle of power supplied to the metering conveyor 545 is increased at S640, thereby increasing the rotational speed of the metering conveyor 545. For example, the duty cycle of power supplied to and/or the rotational speed of the metering conveyor 545 may continue to be increased at S640 while the second sensor 508 remains covered at S660 until the target value is reached at S645.

In at least one example embodiment, if the target value is reached at S645, the method includes determining whether the second sensor 508 is covered at S650. If the second sensor 508 is covered at S650, the method continues to determine whether the second sensor 508 is covered at S650. If the sensor is not covered at S650, the method proceeds to S655 where the duty cycle of power supplied to the metering conveyor 545 is decreased. For example, the rotational speed of the metering conveyor 545 may be decreased at S655. The duty cycle of power supplied to and/or the rotational speed of the metering conveyor 545 may be decreased at S655 due to the flow of agricultural material through the second bypass 300 decreasing and in order to maintain a steady flow of the agricultural material through the second bypass 300.

Returning to S645 and S660, if the target value is not reached at S645 and the second sensor 508 is not covered at S660, then the duty cycle of power supplied to and/or the rotational speed of the metering conveyor 545 may be decreased at S655. After decreasing the duty cycle of power supplied to and/or the rotational speed of the metering conveyor 545 at S655, the wait time is increased at S665.

In at least one example embodiment, the method includes determining whether the starting value of the duty cycle of power and/or the starting speed of the metering conveyor 545 has been reached at S670. For example, the starting value of the duty cycle of power may be the value of the duty cycle of power supplied at S610. If the starting value of the duty cycle of power and/or the starting speed is not reached at S670, the method returns to S660. If the starting value of the duty cycle of power and/or the starting speed is reached at S670, the method returns to S605. In at least one example embodiment, the method continues until the harvesting operation is completed or is ended and/or the flow of agricultural material through the second bypass 300 has stopped.

The various operations of methods described above may be performed by any suitable device capable of performing the operations, such as the controller 565. For example, the operations of methods described above may be performed by various hardware and/or software implemented in some form of hardware (e.g., processor, ASIC, etc.). The software may comprise an ordered listing of executable instructions for implementing logical functions, and may be embodied in any "processor-readable medium" for use by or in connection with an instruction execution system, apparatus, or device, such as a single or multiple-core processor or processor-containing system.

The blocks or operations of a method or algorithm and functions described in connection with some example embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium (e.g., a memory).

According to some example embodiments, the memory may each be a tangible, non-transitory computer-readable medium, such as a Random Access Memory (RAM), a flash memory, a Read Only Memory (ROM), an Electrically Programmable ROM (EPROM), an Electrically Erasable Programmable ROM (EEPROM), registers, a hard disk, a removable disk, a Compact Disk (CD) ROM, any combination thereof, or any other form of storage medium known in the art. In at least one example embodiment, the memory is configured to store the starting duty cycle of power and the target duty cycle of power for each type of agricultural material being harvested. For example, the starting duty cycle of power for canola may be about 30% and the target duty cycle of power for canola may be about 50%. The starting duty cycle of power for wheat may be about 50% and the target duty cycle of power for wheat may be about 90%. The starting duty cycle of power for corn may be about 70% and the target duty cycle of power for canola may be about 100%.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. An apparatus for analyzing agricultural material comprising:

a housing defining an inlet adjacent a first end of the housing and configured to receive the agricultural material, wherein the housing is configured to separate the agricultural material into a first flow and a second flow, the first flow comprising a first density, the second flow comprising a second density, the first density being greater than the second density, the housing is configured to direct the first flow of the agricultural material along a first side of the housing, and the housing is configured to direct the second flow of the agricultural material along a second side of the housing opposite the first side;

a first chamber coupled to the inlet;

a first outlet coupled to the first chamber;

a second chamber coupled to the first chamber, the second chamber being positioned downstream of the first chamber and including a metering conveyor;

a funnel portion between the first chamber and the second chamber; and a second outlet adjacent a second end of the housing and coupled to the second chamber, wherein the first outlet is configured to discharge at least a portion of the agricultural material from the housing and bypassing the second chamber.

2. The apparatus of claim 1, further comprising:

a first sensor coupled to the first side of the housing.

3. The apparatus of claim 2, wherein the first sensor comprises a camera.

4. The apparatus of claim 2, further comprising:

at least one second sensor coupled to the second side of the housing.

5. The apparatus of claim 4, wherein the at least one second sensor comprises one or more of a moisture sensor, a near-infrared (NIR) sensor, a temperature sensor, a capacitive sensor, and a proximity sensor.

6. The apparatus of claim 1, further comprising a wall extending along at least a portion of the metering conveyor from the first side towards the second side of the housing, wherein the funnel portion is defined by at least a portion of the wall.

7. The apparatus of claim 1, wherein a width of the funnel portion tapers between the first chamber and the second chamber.

8. The apparatus of claim 1, wherein the first outlet is coupled to the second outlet.

9. The apparatus of claim 1, wherein the metering conveyor includes a metering wheel, an auger, or a roller.

10. An apparatus for analyzing agricultural material comprising:

a housing defining an inlet adjacent a first end of the housing and configured to receive the agricultural material;

a first chamber coupled to the inlet;

a first outlet coupled to the first chamber;

a second chamber coupled to the first chamber, the second chamber being positioned downstream of the first chamber and including a metering conveyor;

a funnel portion between the first chamber and the second chamber; and a second outlet adjacent a second end of the housing and coupled to the second chamber, wherein the first outlet is configured to discharge at least a portion of the agricultural material from the housing and bypassing the second chamber, wherein the housing is configured to direct the agricultural material within the first chamber on a first side of the housing towards the second outlet at an increased rate compared to the agricultural material on a second side of the housing opposite the first side.

11. A system for analyzing agricultural material comprising:

an elevator including a first side and a second side, the elevator extending from a first end to a second end, the first end of the elevator including a receptacle formed between the first side and the second side, the receptacle configured to receive the agricultural material; and a first housing coupled to the elevator, the first housing defining a first inlet configured to receive at least a portion of the agricultural material, the first housing including, a first chamber coupled to the first inlet, a first outlet coupled to the first chamber, a second chamber coupled to the first chamber, the second chamber being positioned downstream of the first chamber and including a first metering conveyor, a first funnel portion between the first chamber and the second chamber, and a second outlet coupled to the second chamber, wherein the first outlet is configured to discharge at least a portion of the agricultural material from the first housing and bypassing the second chamber, wherein the first housing is configured to separate the agricultural material into a first flow and a second flow, the first flow comprising a first density, the second flow comprising a second density, the first density being greater than the second density, the first housing is configured to direct the first flow of the agricultural material along a first side of the first housing, the first housing is configured to direct the second flow of the agricultural material along a second side of the first housing opposite the first side, and the first housing is configured to direct the agricultural material on the first side of the first housing towards the second outlet at an increased rate compared to the agricultural material on the second side of the first housing.

12. The system of claim 11, wherein the elevator includes a plurality of paddles configured to deliver at least a portion of the agricultural material from the receptacle to the first inlet of the first housing via the first side of the elevator.

13. The system of claim 11, further comprising:

a first sensor coupled to the first side of the first housing.

14. The system of claim 13, wherein the first sensor comprises a camera.

15. The system of claim 11, further comprising:

at least one second sensor coupled to the second side of the first housing.

16. The system of claim 15, wherein the at least one second sensor includes one or more of a moisture sensor, a near-infrared (NIR) sensor, a temperature sensor, a capacitive sensor, and a proximity sensor.

17. The system of claim 11, wherein the first outlet and the second outlet are configured to direct at least a portion of the agricultural material to the receptacle of the elevator.

18. The system of claim 11, wherein the first funnel portion is defined by at least a portion of a wall of the first housing extending along at least a portion of the first metering conveyor from the first side of the first housing towards the second side of the first housing opposite the first side.

19. A system for analyzing agricultural material comprising:

an elevator including a first side and a second side, the elevator extending from a first end to a second end, the first end of the elevator including a receptacle formed between the first side and the second side, the receptacle configured to receive the agricultural material;

a first housing coupled to the elevator, the first housing defining a first inlet configured to receive at least a portion of the agricultural material, the first housing including, a first chamber coupled to the first inlet, a first outlet coupled to the first chamber, a second chamber coupled to the first chamber, the second chamber including a first metering conveyor, a first funnel portion between the first chamber and the second chamber, and a second outlet coupled to the second chamber;

a second housing configured to be coupled to the elevator, the second housing including, a second inlet configured to receive at least a portion of the agricultural material, a third chamber coupled to the second inlet, a third outlet coupled to the third chamber, a fourth chamber coupled to the third chamber, the fourth chamber including a second metering conveyor, a second funnel portion between the third chamber and the fourth chamber, and a fourth outlet coupled to the fourth chamber;

at least one sensor coupled to an exterior of the second housing adjacent the third chamber, the at least one sensor configured to detect a fill level of the second housing; and a conduit configured to be coupled between the second side of the elevator and the second inlet of the second housing, the conduit configured to deliver at least a portion of the agricultural material from the second side of the elevator to the second inlet of the second housing.

* * * * *